United States Patent [19]

Horton et al.

[11] 4,201,773
[45] May 6, 1980

[54] 7-O-(2,6-DIDEOXY-α-L-LYXO-HEX-OPYRANOSYL)-DAUNOMYCINONE, DESMETHOXY DAUNOMYCINONE, ADRIAMYCINONE, AND CARMINOMYCINONE

[75] Inventors: Derek Horton, Columbus, Ohio; Wolfgang Weckerle, Messel; Ernst F. Fuchs, Freiburg, both of Fed. Rep. of Germany; Tak M. Cheung, Sydney, Australia; Beat Winter, Berkeley, Calif.; Roderick J. Sorenson, Ann Arbor, Mich.

[73] Assignee: The United States of America as represented by the Department of Health, Education and Welfare, Washington, D.C.

[21] Appl. No.: 928,252

[22] Filed: Jul. 26, 1978

[51] Int. Cl.² ............... A61K 31/71; C07H 15/24
[52] U.S. Cl. ............................. 424/180; 536/17 A
[58] Field of Search ............... 536/17, 17 A; 424/180

[56] References Cited
U.S. PATENT DOCUMENTS

| 3,590,028 | 6/1971 | Arcamone et al. | 536/17 A |
| 3,803,124 | 4/1974 | Arcamone et al. | 536/17 A |
| 4,046,878 | 9/1977 | Patelli et al. | 536/17 A |
| 4,058,519 | 11/1977 | Arcamone et al. | 536/17 A |
| 4,067,968 | 1/1978 | Lazzari et al. | 536/17 A |
| 4,067,969 | 1/1978 | Penco et al. | 536/17 A |

FOREIGN PATENT DOCUMENTS

| 1161278 | 8/1969 | United Kingdom | 536/17 A |
| 1217133 | 12/1970 | United Kingdom | 536/17 A |

OTHER PUBLICATIONS

Fuchs et al., "Carbohydrate Research", vol. 57, 1977, C36–C39.
Cheung et al., "Carbohydrate Research", vol. 58, 1977, pp. 139–151.

Primary Examiner—Johnnie R. Brown
Attorney, Agent, or Firm—John S. Roberts, Jr.

[57] ABSTRACT

A series of compounds showing high antileukemic activity against P388 murine leukemia and increased aqueous solubility due to substitution of —OH for the known —NH₂ at the 3' position of the hexopyranose sugar, i.e., daunosamine.

These compounds are coupled products of aglycon selected from daunomycinone, desmethoxy daunomycinone, adriamycinone and carminomycinone. These compounds are coupled at the O-7 position of the aglycon with an α-L-lyxo hexopyranose sugar, which sugar isomer particularly sustains or potentiates the biological activity of the coupled compound as well as ameliorates the dose related cardiotoxicity of the parent and known compounds set out below:

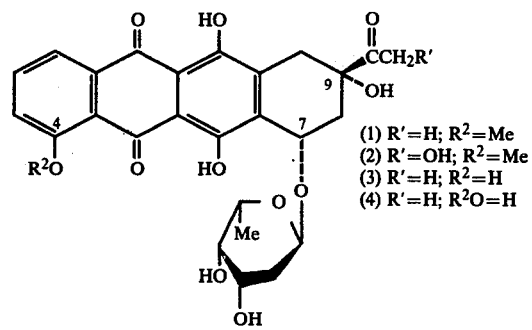

(1) R'=H; R²=Me
(2) R'=OH; R²=Me
(3) R'=H; R²=H
(4) R'=H; R²O=H

11 Claims, No Drawings

7-O-(2,6-DIDEOXY-α-L-LYXO-HEXOPYRANOSYL)-DAUNOMYCINONE, DESMETHOXY DAUNOMYCINONE, ADRIAMYCINONE, AND CARMINOMYCINONE

This invention relates to a series of compounds showing high antileukemic activity against P388 murine leukemia and increased aqueous solubility due to substitution of —OH for the known —NH$_2$ at the 3' position of the hexopyranose sugar; i.e., daunosamine.

These compounds are coupled products of aglycon selected from daunomycinone, desmethoxy daunomycinone, adriamycinone and carminomycinone. These compounds are coupled at the 0-7 position of the aglycon with a α-L-lyxo hexopyranose sugar, which sugar isomer particularly sustains or potentiates the biological activity of the coupled compound as well as ameliorates the dose related cardiotoxicity of the parent and known compounds set out below:

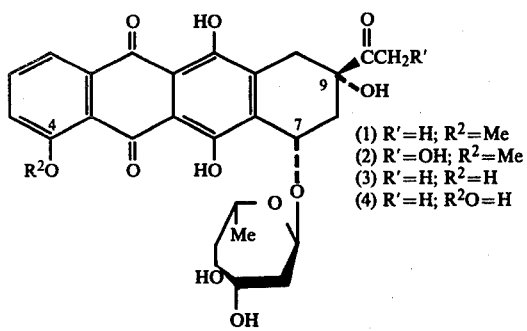

(1) R'=H; R$^2$=Me
(2) R'=OH; R$^2$=Me
(3) R'=H; R$^2$=H
(4) R'=H; R$^2$O=H

The anthracycline or anthraquinone compounds which are the subject of this invention are closely related in structure to natural products illustrated by daunorubicin (daunomycin), desmethoxy daunorubicin, adriamycin, and carminomycin, and the structure of the new compounds is given in the formula above.

In nature the parent compounds have shown antibiotic and antileukemic activity when coupled or joined to sugar molecules. For example, daunorubicin is coupled at the 7 position with an amino sugar daunosamine and in similar fashion there may be coupled adriamycin and carminomycin. The anthracycline compound or fraction which participates in the coupling is termed an aglycon. It is noted that aglycon may be defined as a non-sugar hydrolytic product of a glycoside.

A preferred sugar structure which may be utilized with any of the present related anthracyclines may be denoted as 3'-hydroxy-3'-deamino daunorubicin (NSC 284682) when coupled with daunorubicin and the spelling may be alternately desamino for deamino.

The coupling ties through the 7 position of the anthracycline aglycon structure to the 1' position of the hexopyranose sugar.

PRIOR ART STATEMENT

Patents

U.S. Pat. No. 4,058,519 Arcamone et al teaches adriamycin derivatives and reactive intermediates, for example, 1-halo-2,3,6-trideoxy-3-trifluoroacetamido-4-trifluoroacetoxy-α-L-lyxo (or arabino)hexopyranoses.

U.S. Pat. No. 4,046,878 Patelli et al indicates that the reaction proceeds from daunomycin analogs and uses as a sugar the 1-chloro-2,3,6-trideoxy-3-trifluoroacetamido-4-trifluoroacetoxy-α-L-lyxo pyranose.

Additionally, the following patents are of interest: U.S. Pat. No. 3,590,028 Arcamone et al, U.S. Pat. No. 3,803,124 Arcamone et al, U.S. Pat. No. 4,067,968 Lazzari et al, U.S. 4,067,969 Penco et al, British Pat. No. 1,161,278, and British 1,217,133. The above series of U.S. and British patents are all assigned to the Societa Farmaceutici Italia.

Liturature

Fuchs, et al, *Carbohydrate Research,* 57 (1977), C36–C39.

Cheung et al, *Carbohydrate Research,* 58 (1977), 139–151.

THE SUGARS

The compounds of the present invention differ from the natural products as found in nature in that the 3' amino has been substituted by a hydroxyl group in the basic hexopyranose structure. It has further been found that, of the deamino (desamino) sugars which have isomeric forms of lyxo, ribo, and arabino, the α-L-lyxo anomer shows special antileukemic activity in mice and these α-L-lyxo hexose sugars have been found to have greater aqueous solubility coupled with a biological activity which appears to ameliorate the dose related cardio toxicity present in the natural products. A preferred sugar fraction for this invention is 2,6-dideoxy-α-L-lyxo-hexopyranose which is also known as 2-deoxy-α-L-fucose.

THE BIOLOGICAL EFFECT

The anthracycline antibiotics daunorubicin (1), adriamycin (2), and carminomycin (3) are potent and clinically useful antitumor agents. Their scarcity and certain undesirable side effects common to many antitumor drugs (such as bone-marrow damage, stomatitis, and alopecia), but, in particular, a cumulative, dose-related cardiotoxicity, have limited their broader utilization in chemotherapy.

Derivatives of the natural products which are set out in this invention as well as several semi-synthetic anthracyclines have been prepared and some of these appear to display significant antitumor activity in animals with less toxicity than the parent natural products.

In particular, the compound 7-0-(2,6-dideoxy-α-L-lyxo-hexopyranosyl)daunomycinone (5) was prepared and which is a compound identical to the parent daunorubicin (1) except for replacement of the amino function in the sugar moiety by a hydroxyl group.

Certain compounds included in this invention have shown superior results when tested against P388 mouse leukemia by standard tests such as are set out in Protocol 11 of the Cancer Chemotherapy Reports of May 24, 1972, National Institutes of Health. Values for the deamino daunorubicin (daunomycin) coupled product (NSC 284682) ranged from T/C of 183 for 150 mg, 156 for 100 mg, and 125 for 25 mg against P388 mouse leukemia in tests extending up to 22 days. The analogous peracetylated compound (NSC 283158) also gave superior results against P388 mouse leukemia in tests extending up to 22 days in values showing T/C of 186 at 200 mg and 155 at 100 mg.

GENERALIZED METHOD—PREPARATION OF THE SUGAR INTERMEDIATE PRODUCT

Referring to the diagram below, methyl 4,6-O-benzylidene-2-deoxy-α-D-ribo-hexopyranoside (1) is converted into methyl 3,4-di-O-benzoyl-6-bromo-2,6-dideoxy-α-D-ribohexopyranoside (3) via the 3-O-benzoyl derivative (2) of 1 by subsequent treatment with N-bromosuccinimide. Compound 3 is a key intermediate in high-yielding, preparative syntheses of the title dideoxy sugars, which are constituents of many antibiotics. Dehydrohalogenation of 3 affords the 5,6-unsaturated glycoside 7, which undergoes stereospecific reduction by hydrogen with net inversion at C-5 to give methyl 3,4-di-O-benzoyl-2,6-dideoxy-β-L-lyxo-hexopyranoside (8), whereas reductive dehalogenation of 3 provides the corresponding D-ribo derivative 4. The unprotected glycosides 9 (L-lyxo) and 5 (D-ribo) are readily obtained by catalytic transesterification, and mild, acid hydrolysis gives the crystalline sugars 10 (L-lyxo) and 6 (D-ribo) in 45 and 57% overall yield from 1 without the necessity of chromatographic purification at any of the steps.

The preparation of the final coupled product (NSC 284682) and the diacetyl product as for daunomycinone are set out post in the examples.

$\delta$ 6.27 (dd, $J_{1,2e}$ 1.5, $J_{1,2a}$ 3.5 Hz, H-1 of α anomer), 5.80 (dd, $J_{1,2e}$ 5, $J_{1,2a}$ 7 Hz, H-1 of β-anomer), 5.40–4.96 (m, H-3,4), 4.18 (q, $J_{5,6}$ 6.8 Hz, H-5 of α anomer), 3.85 (q, $J_{5,6}$ 6.4 Hz, H-5 of β anomer), 2.35–1.70 (m, H–2e, 2a, partly obscured by O-acetyl signals), 2.12, 2.08, 2.07, and 1.96 (4s, OAc), 1, 17 (d, H-6 of β anomer), and 1.10 (d, H-6 of α anomer).

The key intermediate for the glycosidation of daunomycinone, namely, 3,4-di-O-acetyl-2,6-dideoxy-α-L-lyxo-hexopyranosyl chloride (8), was obtained as a syrup in theoretical yield by treatment of 7, dissolved in anhydrous ether, with dry hydrogen chloride at 0°; $^1$H-n.m.r. (chloroform-d): $\delta$ 6.32 (dd, 1H, $J_{1,2e}$ 1.5, $J_{1,2a}$ 3.7 Hz, H-1), 5.47 (ddd, 1 H, $J_{2a,3}$ 11.5, $J_{2e,3}$ 3, $J_{3,4}$ 5.2 Hz, H-3), 5.26 (m, 1 H, H-4), 4.36 (dq, 1H, $J_{4,5}$ 1.5, $J_{5,6}$ 6.8 Hz, H-5), 2.38 (ddd, 1 H, $J_{2e,2a}$ 12.4 Hz, H-2a), ~2.10 (m, 1 H, obscured by O-acetyl signals, H-2e), 2.10, 1.94 (2s, 3 H each, OAc), and 1.13 (d, 3 H, H-6).

When daunomycinone (1 molar equiv.) in anhydrous dichloromethane was treated with 8 (2 molar equiv.) under Koenigs-Knorr conditions (yellow mercuric oxide, mercuric bromide) in the presence of molecular sieve 4A for 24 h at 22°, only one product ($R_F$ 0.55) was detected by t.l.c. on silica gel in 4:3:3 benzene-acetone-ether; it was observed as a red spot under u.v. and visible light and was contaminated with faster-migrating,

SCHEME 1

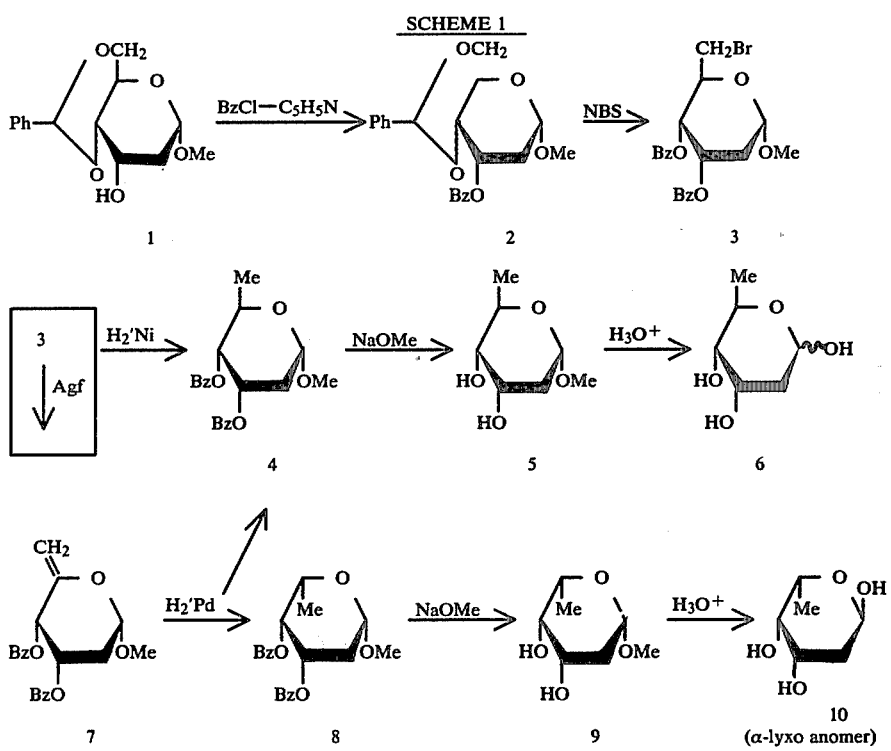

EXAMPLE 1

Preparation of 7-O-(2,6-dideoxy-α-L-lyxo-hexopyranosyl)-daunomycinone (5)

Peracetylation (pyridine-acetic anhydride, 2 days at 0°) of crystalline 2,6-dideoxy-α-L-lyxo-hexose (6) afforded, in quantitative yield, the triacetate 7 as a 2:1 mixture of the α and β anomers. The former could be isolated pure by fractional crystallization (ethanol-hexane): m.p. 112°, $[\alpha]_D$ −137° (c 0.7, chloroform); $^1$H-n.m.r. data for the anomeric mixture (in chloroform-d):

sugar impurities. The excess of 8 was decomposed by adding methanol, the inorganic material was filtered off, and the solvent evaporated. Column chromatography on silica gel, using as eluant first 4:1 ether-petroleum ether (to remove the impurities) and then 2:3 benzene-acetone, afforded 7-O-(3,4-di-O-acetyl-2,6-dideoxy-α-L-lyxo-hexopyranosyl)daunomycinone (4) as an amorphous (diffuse X-ray powder diffraction pattern) solid in 84% yield (based on daunomycinone), whose analysis indicated 4.0.5 $H_2O$); m.p. 134°–138°, $[\alpha]_D + 344°$ (c 0.03, methanol); $\lambda_{max}^{MeOH}$ 235 nm ($\epsilon_{mM}$ 27.1), 257 (23.9), 270 (10.9), 292 (8.5), 474 (12.6), 495 (12.8), and 534 (6.9); $\nu_{max}$ 3490 (OH), 1750 (O-acetyl), 1720 (C-acetyl), 1620 and 1580 cm$^{-1}$ (chelated quinone). The $^1$H n.m.r. spectrum of 4 (in chloroform-d) was nearly identical with that of N-acetyldaunorubicin, except for the absence of an NH resonance and the paramagnetic shift of the signal for H-3' (as anticipated for the replacement of the acetamido group in the latter by an acetoxy substituent at C-3' in 4). The α configuration of the glycosidic linkage was readily verified by inspection of the signal for the anomeric proton at δ 5.57 (broad s, v ½=7 Hz).

Deacetylation was accomplished by treating a methanolic solution of 4 (200 mg/10 ml) with a catalytic amount of sodium methoxide for 30 h at 22°. De-ionization [Amberlite IRC-50 (OH$^+$) for 4 h at 0°] followed by evaporation of the solvent afforded crude 7-O-(2,6-dideoxy-α-L-lyxo-hexopyranosyl)daunomycinone (5), which was recrystallized from acetone to yield pure, crystalline (X-ray powder diffraction pattern) 5 in two crops (79%); m.p. 252°-254°, $[\alpha]_D + 219°$ (c 0.03, methanol); $\lambda_{max}^{MeOH}$ 235 nm ($\epsilon_{mM}$ 28.8), 254 (25.9), 272 (10.3), 292 (8.8), 474 (12.3), 497 (12.3), and 534 (6.4); $\nu_{max}$ 3470 (very broad, OH), 1715 (C-acetyl), 1620 and 1580 cm$^{-1}$ (chelated quinone.

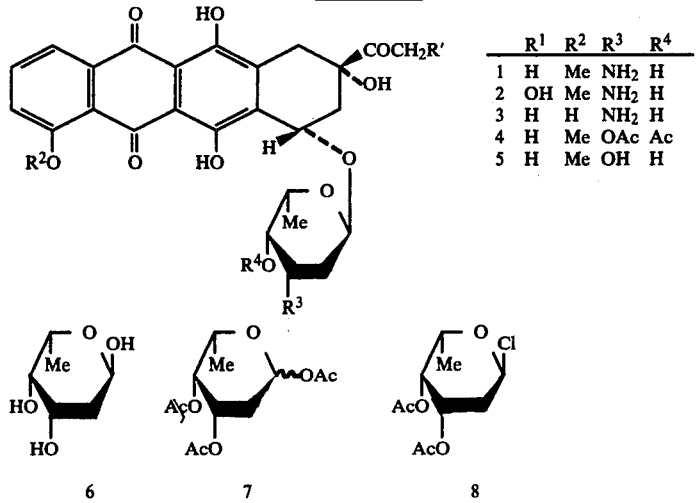

SCHEME 2

EXAMPLE 2

Preparative Syntheses of the Intermediate 2,6-Dideoxy-α-L-lyxo-Hexose (2-Deoxy-α-L-Fucose)

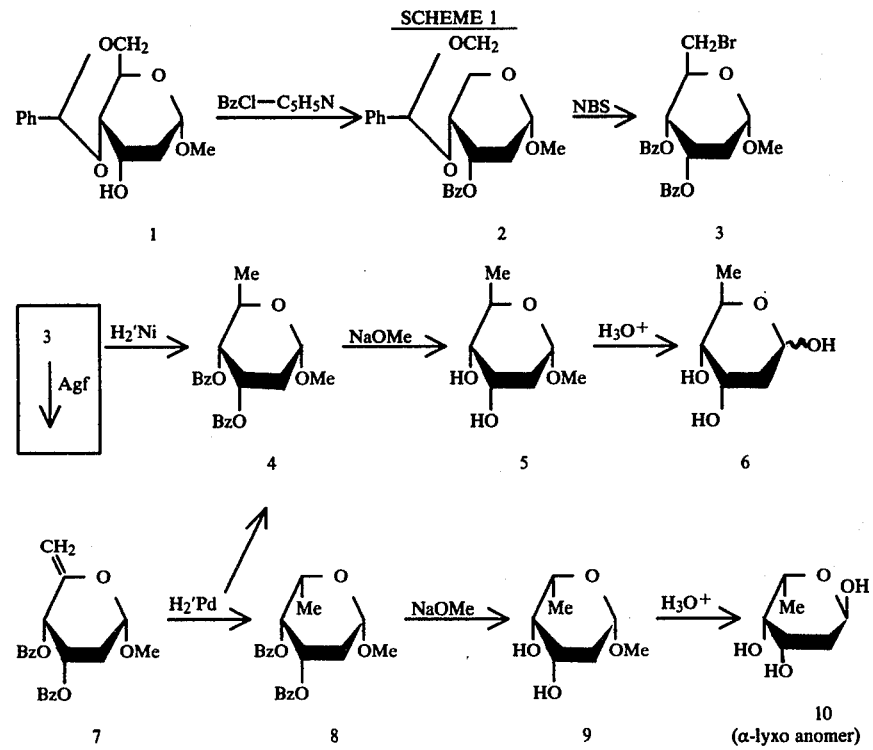

SCHEME 1

Referring to the diagram above, methyl 4,6-O-benzylidene-2-deoxy-α-D-ribo-hexopyranoside (1) was converted into methyl 3,4-di-O-benzoyl-6-bromo-2,6-dideoxy-α-D-ribo-hexopyranoside (3) via the 3-O-benzoyl derivative (2) of 1 by subsequent treatment with N-bromosuccinimide. Compound 3 is a key intermediate in high-yielding, preparative syntheses of the dideoxy sugars, which are constituents of many antibiotics. Dehydrohalogenation of 3 afforded the 5,6-unsaturated glycoside 7, which underwent stereospecific reduction by hydrogen with net inversion at C-5 to give methyl 3,4-di-O-benzoyl-2,6-dideoxy-β-L-lyxo-hexopyranoside (8), whereas reductive dehalogenation of 3 provided the corresponding D-ribo derivative 4. The unprotected glycosides 9 (L-lyxo) and 5 (D-ribo) were readily obtained by catalytic transesterification, and mild, acid hydrolysis gave the crystalline sugars 10 (L-lyxo) and 6 (D-ribo) in 45 and 57% overall yield from 1 without the necessity of chromatographic purification at any of the steps.

The L-lyxo analog 10 which is the enantiomorph of the naturally occurring dideoxy sugar oliose crystallized in the α-L-form as evidenced by its mutarotation in water and acetone. The final specific rotation showed good correlation with that recorded for the synthetic and natural product. In the last step of the production of the intermediate, the following specific experimental method was followed.

2,6-dideoxy-α-L-lyxo-hexose (2-deoxy-α-L-fucose, α-L-oliose, 10): A solution of the methyl glycoside 9 (990 mg, 6.10 mmol) in acetic acid (3 ml) and water (12 ml) was boiled for 30 min under reflux, at which time t.l.c. (19:1 ethyl acetate-methanol) indicated that hydrolysis of the glycoside was com-lete. The solvent was evaporated off, and water (three successive 10-ml portions) was added to the concentrated solution (~2 ml) and evaporated after each addition to remove all of the acetic acid. Finally, the solution was evaporated to dryness to afford a colorless, hydroscopic syrup (10; $R_F$ 0.29) that was dried over phosphorus pentaoxide and potassium hydroxide for several days; yield 890 mg (98%). Addition of a little acetone effected crystallization and the crystals (10) were filtered off in an inert atmosphere (nitrogen) and dried; yield 360 mg, m.p. 102°–105°, $[\alpha]_D^{23}$ −97 (initial, extrapolated)→ −81.2 (4 min)→ −73.8 (6 min)→ −64.8 (10 min)→ −51.5° (2 h, equil.; c 1.04, water) and −134 (initial, extrapolated)→ −131.1 (750 min)→ −128.3 (15 min)→ −122.7 (30 min)→ −75.6° (10 h, equil.; c 0.99, acetone); X-ray powder diffraction data: 7.93 s (3), 6.78 w, 6.12 vs (2), 5.37 m, 4.82 W, 4.31 vs (1), 4.12 m, 3.94 m, 3.72 w, and 3.48 m.

Anal. Calc. for $C_6H_{12}O_4$ (148.16): C, 48.64; H, 8.16. Found: C, 48.65; H, 8.37.

EXAMPLE 3

Preparation of 7-O-(3,4-di-O-acetyl-2,6-dideoxy-α-L-lyxo-hexopyranosyl)daunomycinone, 4 (NSC 283158)

General method. I.R. spectra were recorded with a Perkin-Elmer Model 457 Grading i.r. spectrophotometer. $^1$H-N.m.r. spectra were recorded at 100 MHz with a Varian HA-100 spectrometer with tetramethylsilane (δ=0.00) as internal standard. U.V.-visible spectra were recorded with a Cary Model 170 u.v.-visible spectrophotometer. T.L.C. was performed on precoated plates of Silica Gel 60 (E. Merck). Zones of colorless compounds were detected by spraying with sulfuric acid and subsequent heating. Mass spectra were recorded with an AE1 M-9 double focusing, high-resolution spectrometer. Melting points are uncorrected. X-Ray powder diffraction data give interplanar spacings, Å, for Cukα radiation. The camera diameter was 114.59 mm. Relative intensities were estimated visually.

1,3,4-tri-O-acetyl-2,6-dideoxy-α-and β-L-lyxo-hexopyranose (11 and 12). Treatment of crystalline 2,6-dideoxy-α-L-lyxo-hexose (10; 7.41 g, 50 mmol) with 1:2 acetic anhydride-pyridine (120 ml) for 18 at ~25° afforded, after conventional processing, a syrup, 2:1 mixture (as judged from n.m.r. data) of the anomeric peracetates 11 and 12; yield 13.7 g (theoretical). The preponderant product, the α anomer 11, was isolated pure by fractional crystallization from ethanol-hexane: mp 112°, $[\alpha]_D^{23}$ −137° (c 0.7, chloroform); MS m/e 274 (M+, absent), 215 (0.8, M+−AcO.), 172 (0.6), 171 (0.6), 170 (5), 155 (3.8), 154 (4, M.+−2HOAc), 145 (4), 144 (1.2), 139 (1.8), 129 (0.9), 128 (5), 115 (1.9), 113 (1.9), 112 (7), 111 (1.1), 103 (8), 102 (2.9), 97 (8), 96 (5), 95 (13), 87 (2.7), 82 (4.8), 81 (16), 78 (4), 73 (3.6), 69 (2.6), 68 (23), 67 (6), 66 (2), 65 (2.3), 60 (8), 58 (3.9), 57 (3.6), 53 (5), 52 (1.7), 51 (2.5), 50 (2), 46 (2), 45 (8), 44 (13), 43 (100), and 42 (32); X-ray powder diffraction data: 10.71 m (4), 8.46 vs, 6.88 vs (1,1), 5.98 m (5,5,5), 5.43 s (2,2,2), 5.03 vs (1,1), 4.45 m (5,5,5), 4.31 m (5,5,5), 3.90 s (3), 3.79 s (2,2,2), 3.62 s (2,2,2), and 3.43 w. Anal. ($C_{12}H_{18}O_7$) C, H.

The peracetates 11 and 12, prepared from a hydrolyzate of cinerubine A, were reported to have m.p. 109°–110°, $[\alpha]_D$ −137° in chloroform, and m.p. 67°–70°, $[\alpha]_D$ −39° in chloroform, respectively.

3,4-di-O-acetyl-2,6-dideoxy-α-L-lyxo-hexopyranosyl chloride (13). A stream of dry hydrogen chloride was passed for 10 min into a cold (0°) solution of syrup 11 and 12 (4.16 g, 15.2 mmol) in dry ether (2.50 ml). After 18 h at +5°, the solvent was removed under diminished pressure (bath temp. <30°) to give the chloride 13 in quantitative yield (3.7 g) as a pale, yellow syrup that was subjected, without delay, to the coupling reaction described next.

7-O-(3,4-di-O-acetyl-2,6-dideoxy-α-L-lyxo-hexopyranosyl)daunomycinone 4 (NSC 283158). A mixture of the chloride 13 (1.8 g, 7.18 mmol), daunomycinone (796 mg, 2.0 mmol), yellow mercuric oxide (1.65 g, 7.62 mmol), mercuric bromide (500 mg, 1.39 mmol), and granular molecular sieve 4A (15 g) in anhydrous dichloromethane (150 ml) was stirred for 30 h at 22°. TLC (4:3:3 benzene-acetone-ether) revealed at this point that all of the anthraquinone had reacted to form a single product ($R_F$ 0.55) observable as a red spot under u.v. and visible light. The inorganic material was filtered off and thoroughly washed with dichloromethane. The combined filtrates were evaporated and the remaining residue was placed on a short column of silica gel (E. Merck No. 7734, 63–200 μm). Sugar impurities were eluted first with 4:1 ether-petroleum ether and then the product was recovered by eluting the column with 2:3 benzene-acetone and evaporation of the solvet. The crude product was dissolved in ethanol (150 ml) and the clear solution was concentrated to about one fifth its original volume whereupon, after cooling, compound 4 precipitated as an amorphous (diffuse X-ray powder diffraction pattern) solid; yield 970 mg (78%, based on daunomycinone); mp 134°–138°, $[\alpha]_D^{23}$ +344° (c 0.03, methanol); ir $v_{max}^{(KBr)}$ 3490 (OH), 1750 (O-acetyl), 1720 (C-acetyl), 1620 and 1580 cm$^{-1}$ (chelated quinone); uv $\lambda_{max}^{(MeOH)}$ 233 ($\epsilon \times 10^{-3}$ 36.1), 251 (26.8), 288 (9.3), 313 (2.8), 327 (3.4), 388 (2.8), 450 (9.0), 473 (12.2), 480 (12.4), 496 (12.5), 519 (8.1), 532 (7.0), and 578 nm (0.4). The $^1$H-NMR spectrum of 4 (in chloroform-d) was similar to that N-acetyldauorubicin except for the absence of an NH resonance and the paramagnetic shifts of the H-3 and H-4 signals: Anal. ($C_{31}H_{32}O_{13} \cdot 0.5 H_2O$) C, H.

EXAMPLE 4

Preparation of 7-O-(2,6-dideoxy-α-L-lyxo-hexopyranosyl)daunomycinone 5 (NSC 284682)

A. From 4 by catalytic transesterification. To a solution of the protected anthracycline glycoside 4 (620 mg, 1.0 mmol) in abs. methanol (20 ml) was added M sodium methoxide (200 ml) and the mixture was kept for 12 h at 25°. TLC (2:3 benzene-acetone) indicated the reaction to be complete ($R_F$ 0.4). Methanol (400 ml) was then added to the dark-blue solution, which was then treated with Amberlite IRC-50 (H+) (4 ml, 4 h, 0°) whereupon the color changed to red. Evaporation of the solvent afforded crude 5 that was recrystallized from acetone-hexane; yield 360 mg (68%); mp 252°–254°, $[\alpha]_D^{22}$ +219° (c 0.03, methanol) ir $\nu_{max}^{(KBr)}$ 3470 (very broad, OH), 1715 (C-acetyl), 1620 and 1580 cm$^{-1}$ (chelated quinone); uv $\lambda_{max}^{(MeOH)}$ 233 ($\epsilon \times 10^{-3}$ 35.4), 251 (25.6), 288 (9.1), 313 (2.6), 327 (3.2), 385 (2.5), 449 (8.5), 473 (1t.9), 480 (12.1), 497 (12.4), 517 (8.6), 532 (7.0), and 580 nm (0.5). X-ray powder diffraction data: 12.02 m (2), 10.52 vw, 7.89 m (1), 6.94 vw, 6.00 w (5,5), 5.02 vs, 4.77 w (6), 4.31 vw, 4.14 vw, 3.86 m (3), 3.40 w (5,5), and 1.95 m (4). Anal. ($C_{27}H_{28}O_{11}$) C, H.

B. Alternative preparation of 5: preparative-scale glycosidation saponification. A mixture of daunomycinone (4.0 g, 10 mmol), yellow mercuric oxide (12.7 g), mercuric bromide (3.7 g), and molecular sieve (3A, 50 g) in anhydrous dichloromethane (500 ml) was stirred for 1 h at 15°. A solution of the chloride 13 (5.0 g, 20 mmol) in anhydrous dichloromethane (50 ml) was then added. TLC (2:3 benzene-acetone) after 90 min indicated reaction to be complete. The mixture was filtered and the inorganic filter-cake washed thoroughly with dichloromethane. The combined filtrates were successively washed with aqueous potassium iodide (30%), aqueous sodium hydrogencarbonate and water, dried (magnesium sulfate), and evaporated. To the residue was added cold (0°)aqueous 0.2 N sodium hydroxide (500 ml) and the suspension was stirred at 0° until a clear, violet solution had been formed (~2 h). The pH then was adjusted to 6 by careful addition of M hydrochloric acid with ice cooling. The clear red solution was saturated with sodium chloride and kept overnight at 5°. Compound 5 precipitated, was collected by filtration, dried over phosphorus pentaoxide in vacuo and recrystallized from dichloromethane-hexane to give pure 5 (4.77 g, 90%).

EXAMPLE 5

In biological testing under Protocol 11 of Cancer Chemotherapy Reports, May 24, 1972, National Institutes of Health, the following values were noted in testing against P388 mouse leukemia.

| Compound | NSC No. | Dose (mg/kg) | T/C (%) | No. of toxic deaths No. of mice treated |
|---|---|---|---|---|
| 4 | 283158 | 200 | 186 | |

-continued

| Compound | NSC No. | Dose (mg/kg) | T/C (%) | No. of toxic deaths No. of mice treated |
|---|---|---|---|---|
| 5 | 284682 | 100 | 153 | |
| | | 400 | 89 | 1/5 |
| | | 200 | | 0/5 |
| | | 100 | 156 | 0/5 |
| | | 50 | 183 | 0/5 |
| | | 25 | 125 | 0/5 |

It is noted that a value of 125 or greater for T/C is considered significant antileukemic effect.

We claim:

1. A compound selected from one member of the group of aglycons consisting of daunomycinone, desmethoxy daunomycinone, adriamycinone, and carminomycinone coupled at the 0–7 position to a 3' desamino α-L-lyxo hexose sugar at the 1' position of the sugar molecule according to the following formula:

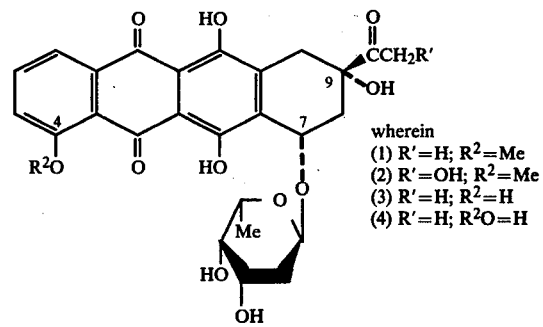

wherein
(1) R'=H; R$^2$=Me
(2) R'=OH; R$^2$=Me
(3) R'=H; R$^2$=H
(4) R'=H; R$^2$O=H 2. The compound according to claim 1 wherein the aglycon utilized is daunomycinone.

3. The compound according to claim 1 wherein the aglycon utilized is desmethoxy daunomycinone.

4. The compound according to claim 1 wherein the aglycon utilized is adriamycinone.

5. The compound according to claim 1 wherein the aglycon utilized is carminomycinone.

6. A method of treating murine leukemia in mice which comprises injecting a mouse infected with P388 leukemia with a biologically palliative amount and in a dosage regimen of up to 22 days of a compound selected from

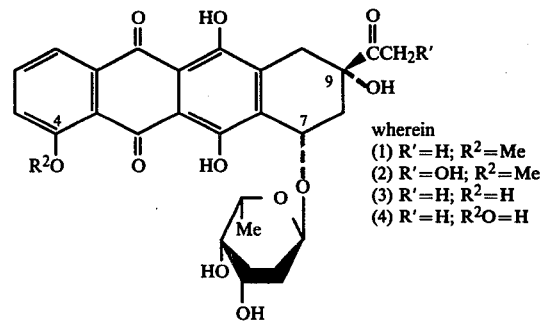

wherein
(1) R'=H; R$^2$=Me
(2) R'=OH; R$^2$=Me
(3) R'=H; R$^2$=H
(4) R'=H; R$^2$O=H 7. The method of claim 6 wherein the aglycon utilized is daunomycinone.

8. The method of claim 6 wherein the aglycon utilized is desmethoxy daunomycinone.

9. The method of claim 6 wherein the aglycon utilized is adriamycinone.

10. The method of claim 6 wherein the aglycon utilized is carminomycinone.
11. The compound according to claim 1 wherein the 3'-desamino α-L-lyxo hexose sugar is in the following configuration
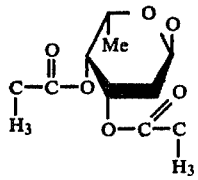
* * * * *